(12) United States Patent
Prokopowicz, III et al.

(10) Patent No.: US 7,125,996 B2
(45) Date of Patent: Oct. 24, 2006

(54) FLUORESCENT PROBES FOR USE IN PROTEIN KINASE INHIBITOR BINDING ASSAY

(75) Inventors: Anthony S. Prokopowicz, III, Stormville, NY (US); Martha Priscilla Brown, Southbury, CT (US); Jessi Marie Wildeson, Thomaston, CT (US); Scott Jakes, Southbury, CT (US); Mark E. Labadia, Brookfield, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/955,129

(22) Filed: Sep. 30, 2004

(65) Prior Publication Data

US 2005/0100978 A1   May 12, 2005

Related U.S. Application Data

(60) Provisional application No. 60/508,539, filed on Oct. 3, 2003.

(51) Int. Cl.
   *C07D 239/30* (2006.01)
   *C07D 233/96* (2006.01)
   *A61K 31/506* (2006.01)
   *C09K 11/06* (2006.01)

(52) U.S. Cl. .................. 544/294; 544/230; 514/275; 252/301.16

(58) Field of Classification Search .............. None
See application file for complete search history.

(56) References Cited

U.S. PATENT DOCUMENTS

| 6,169,106 | B1 | 1/2001 | Heckel et al. |
| 2003/0108910 | A1 | 6/2003 | Toland et al. |
| 2003/0171359 | A1* | 9/2003 | Dahmann et al. ...... 514/217.06 |
| 2004/0058978 | A1 | 3/2004 | Walter et al. |
| 2004/0242613 | A1* | 12/2004 | Cardozo et al. ............. 514/275 |
| 2005/0124640 | A1* | 6/2005 | Cardozo et al. ............. 514/275 |

FOREIGN PATENT DOCUMENTS

WO   WO 03/031606 A2   4/2003
WO   WO 2003032997 A1 *  4/2003

OTHER PUBLICATIONS

A. Janoshazi, et al. "Rapid in Vitro Conformational Changes of the Catalytic Site of PKCalpha Assessed by FIM-1 Fluorescence" Biochemistry 1999, 38, 13316-13327 XP 002317136.
H. Vankayalapati, et al. "Targeting Aurora2 Kinase in Oncogenesis: A Structural Bioinformatics Approach to Target Validation and Rational Drug Design" Molecular Cancer Therapeutics 2003, 2, 283-294 XP002317137.

* cited by examiner

*Primary Examiner*—Kamal A. Saeed
*Assistant Examiner*—Nyeemah Grazier
(74) *Attorney, Agent, or Firm*—Michael P. Morris; Mary-Ellen M. Devlin; David A. Dow

(57) ABSTRACT

The invention provides methods relating to a novel screening assay format that can be applied to broad members of the protein kinase gene family. The assay uses a series of labeled, active site probes described herein that can be displaced by an inhibitor agent. The $K_d$ for the inhibitor compound is derived based on the $K_d$ of the probe for the kinase and the dose response of the inhibitor agent. The invention also provides active site probes suitable for use with the screening method.

3 Claims, 2 Drawing Sheets

Anisotropy plotted as a function of STK12 kinase domain concentration. The probe was held constant at 25 nM. Shown is a regression fit to the data using a single-site binding model. The $K_d$ for the probe binding to STK12 kinase domain was determined to be 161 nM.

Anisotropy plotted as a function of inhibitor concentration. The probe, and STK12 kinase domain were held constant at 25 nM and 200 nM respectively. Shown is a regression fit to the data using a single-site binding model. The $K_d$ for the inhibitor binding to STK12 kinase domain was determined to be 150 nM.

FLUORESCENT PROBES FOR USE IN PROTEIN KINASE INHIBITOR BINDING ASSAY

RELATED APPLICATION

This application claims priority to U.S. provisional application No. 60/508,539, filed on Oct. 3, 2003, the contents of which are incorporated herein.

FIELD OF THE INVENTION

This invention relates generally to a novel screening assay format that can be applied to broad members of the protein kinase gene family and is useful in the detection and evaluation of kinase inhibitors. This invention also relates to novel fluorescent probes used in the assay, and methods of manufacturing such fluorescent probes.

BACKGROUND OF THE INVENTION

Protein kinases play a critical role in the regulation of virtually all aspects of cellular regulation and comprise one of the most active areas of research in the pharmaceutical industry today. The 522 protein kinase domains in the human genome may provide tremendous opportunities for developing new drugs for untreated disease and the development of protein kinase inhibitors has increasingly become a major focus for the pharmaceutical industry. Protein kinase inhibitors have been reported to be useful in the treatment of numerous diseases including cancer, inflammatory and immunological diseases. See for example I. K. Mellinghoff and C. L. Sawyers, Kinase Inhibitor Therapy in Cancer, 14(12):1–11, 2000; J. Dumas, Growth factor receptor kinase inhibitors: recent progress and clinical impact, Current Opinion in Drug Discovery & Development, 4(4):378–89, 2001; J. Dumas, Protein kinase inhibitors: emerging pharmacophores, 1997–2000, Expert Opinion on Therapeutic Patents. 11(3):405–429, 2001; D. H. Williams and T. Mitchell, Latest developments in crystallography and structure-based design of protein kinase inhibitors as drug candidates, Current Opinion in Pharmacology, 2(5):567–73, 2002; S. B. Noonberg and C. C. Benz, Tyrosine kinase inhibitors targeted to the epidermal growth factor receptor subfamily: role as anticancer agents, Drugs, 59(4):753–67, 2000; S. Brunelleschi, L. Penengo, M. M. Santoro and G. Gaudino, Receptor tyrosine kinases as target for anti-cancer therapy, Current Pharmaceutical Design. 8(22):1959–72, 2002; P. G. Goekjian and M. R. Jirousek, Protein kinase C in the treatment of disease: signal transduction pathways, inhibitors, and agents in development, Current Medicinal Chemistry. 6(9):877–903, 1999, A. Gordon, The increasing efficacy of breast cancer treatment, Clinical Oncology (Royal College of Radiologists), 9(5):338–42, 1997.

While this large gene family represents a rich source on new drug targets, developing assays used to determine compound affinity is highly problematic. Current high throughput screening assays for protein kinase inhibitors measure the incorporation of phosphate into a protein or peptide substrate. The most established method for assaying protein kinase inhibitors is a radiometric assay in which the gamma phosphate of ATP is labeled with either $^{32}P$ or $^{33}P$. When the kinase transfers the gamma phosphate to the hydroxyl of the protein substrate during the phosphor-transferase reaction the protein becomes covalently labeled with the isotope. The protein is removed from the labeled ATP and the amount of radioactive protein is determined. This assay is still the gold standard for quantitative protein kinase assays. Adaptation of this assay into a high throughput format is problematic due to the labor intensive separation steps and the large amounts of radioactivity that are used.

An alternative radiometric assay that is capable of higher throughput is the SPA or scintillation proximity assay (Amersham International). In this assay scintillant impregnated beads emit light when the labeled substrate is bound to the bead. This assay is limited by the level of radioactivity and the efficiency of the peptide substrate.

Most non-radioactive assays use antibodies that recognize the product of the kinase reaction, i.e. a phospho-peptide. The binding assays use antibodies detected with enzyme-catalyzed luminescent readout. These methods are limited by reagent availability, well coating, and multiple wash and incubation steps.

Techniques using fluorescence polarization to measure either protein kinase activity or inhibitor binding rely on a labeled antibody or peptide substrate. In these assays the enzyme transfers the gamma phosphate of ATP to a protein or peptide substrate. This activity is monitored by detecting the phosphor-peptide by such means as an antibody. The binding of the antibody to the phosphor-peptide will slow the free rotation of the peptide in solution and, therefore, a polarization signal from the product of the catalytic reaction can be detected. Examples include Burke et al. US 2001/0004522 A1 or T. C. Turek et al., Analytical Biochemistry, 2001, 299 (1), 25–53.

Each of the assays described above determines the affinity of an inhibitor based on reductions in the enzyme's product formation. Despite many alternatives to measure enzyme product, each assay format requires an active enzyme, a high affinity substrate and a specialized antibody to bind to the phospho-peptide. In most cases, obtaining an active enzyme involves phosphorylation of the activation loop which lies across the catalytic cleft. This phosphorylation can be highly problematic when the upstream kinase performing this function is unknown. Even if the activating kinase is known, the requirement necessitates cloning or co-expressing multiple kinases. In some cases, additional cofactors such as the cyclins must be added to fully activate the protein.

Protein kinases display a great deal of sequence specific substrate selection. Therefore, suitable specific substrate must be found for each kinase. In addition, if the substrate site is a serine or threonine then specialized phosphor-specific antibodies must be obtained to monitor activity in a high throughput assay format. These requirements add uncertainty to the design of new kinase assays as well as added expense.

In summary, problems with protein kinase assay development are most often encountered with the activation step and in protein substrate selection. Development of a high throughput screening assay for new protein kinases currently takes 6–12 months. In addition to cloning and expressing the protein the enzyme must be activated, substrates must be found, and reagents to detect the product of the enzyme reaction must be generated. This is a very time consuming and labor intensive effort and each assay must be specialized for one or a small subset of the protein kinases.

Any assay that employs methods to bind phospho-peptide substrate is limited by the concentration of ATP used in the assay. This is inevitable as both the phosphorylated amino acids of the peptide substrate and the phosphates on ATP compete with each other for the binding site on the added reagent. Kinases with medium to high $K_m$ values assayed at sub $K_m$ values make substrate conversion problematic.

Finally, it is desirable to have an assay that expresses compound affinity as Kd rather than $IC_{50}$. This allows for transparent comparison of inhibitors between kinases, critical for determining compound selectivity. One cannot compare $IC_{50}$ measurements from kinase to kinase without additional ATP $K_m$ data.

To overcome these problems it would be desirable to have an assay to measure inhibitor affinities that is compatible with high throughput screening, is homogeneous (no wash steps), does not require activated protein, does not require a catalytic reaction, is substrate independent, is not dependent on ATP concentrations and measures compound $K_d$ values. Such an assay would save institutes and companies involved in drug discovery research millions of dollars by reducing assay development time and the cost of reagents.

SUMMARY OF THE INVENTION

This invention provides a binding assay to measure the affinity of inhibitors to protein kinases. The binding assay was created around a series of labeled, active site probes described below that are used and detected in a fluorescence polarization format. Displacement of the labeled probe by the inhibitor can be used to generate a $K_d$ for the inhibitor to the enzyme.

This invention also provides novel probes for use in a binding assay of inhibitors to protein kinases.

One embodiment of the invention provides an assay for the identification of a kinase inhibitor agent comprising the steps of:
 a) establishing the $K_d$ of an active site probe for an ATP binding site;
 b) contacting the active site probe with protein comprised of a kinase domain and measuring a signal from said probe to establish a base line level signal;
 c) incubating the active site probe: kinase complex with a candidate inhibitor agent and measuring the signal from said probe;
 d) comparing the signal from step b) with the signal from step c);
 e) deriving the $K_d$ for the candidate inhibitor agent based on the $K_d$ of the probe for its ATP binding site and the dose response of the candidate inhibitor agent;

under conditions where the probe can be displaced by the candidate inhibitor and wherein the active site probe binds to the ATP binding domain of said kinase.

In another embodiment of the invention the protein comprising the kinase domain is a full length kinase.

Another embodiment of the invention the probe provides for a fluorescent probe and the signal is measured as a shift in fluorescent polarization of the probe.

Another embodiment of the invention provides an assay using the probe of general formula I described herein.

Another embodiment of the invention provides an assay using the probe of general formula II described herein.

Another embodiment of the invention provides an assay using the probe of general formula III described herein.

In another embodiment of the invention the active site probe is 6-(2,7-difluoro-6-hydroxy-3-oxo-3H-xanthen-9-yl)-N-[6-(5-nitro-2-phenylamino-pyrimidin-4-ylamino)-hexyl]-isophthalamic acid with STK12 kinase domain.

DETAILED DESCRIPTION OF THE INVENTION

Figure 1:
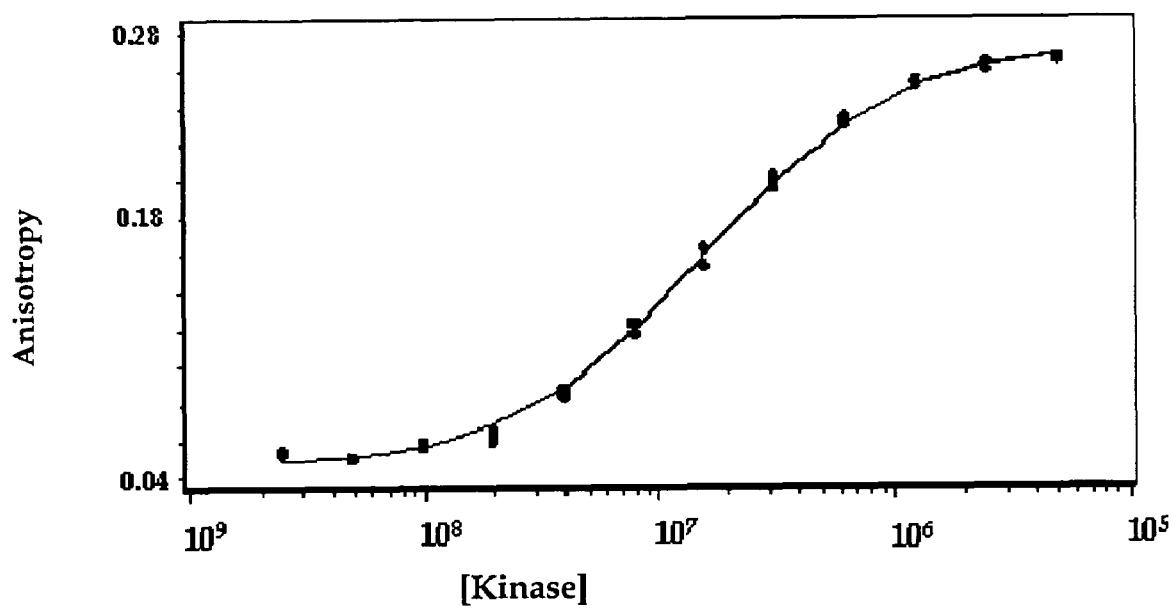
FIG. 1 shows the fluorescence polarization results obtained by titrating the fluorescent probe 6-(2,7-difluoro-6-hydroxy-3-oxo-3H-xanthen-9-yl)-N-[6-(5-nitro-2-phenylamino-pyrimidin-4-ylamino)-hexyl]-isophthalamic acid with STK12 kinase domain.

The present invention is directed to a kinase assay for the detection and evaluation of inhibitors of members of the protein kinase gene family. The new assay format uses active site probes to compete with enzyme inhibitors, thereby eliminating the need for enzyme activation and substrates. Use of this assay method allows inhibitor binding data to be obtained independently of a catalytic assay, thereby, allowing HTS assays to be run with unactivated protein and without substrates. The assay uses a defined set of labeled probes, defined below that can be made at a nominal cost.

I. The Fluorescent Probes

The fluorescent probes of the present invention bind to the active site of a kinase and have the following general formula (I):

$$R_1\text{-L-X—Y} \qquad (I)$$

wherein $R_1$ is the radical of compound that binds to the active site of the kinase, Y is a fluorescent label, L is a one or more atom linker between $R_1$ and X, and X is the functional group that joins L and fluorescent label, Y.

The assay of the present invention is expected to be useful to detect inhibitors of kinase family members. Accordingly, moiety $R_1$ in the fluorescent probe of the present invention would be selected such that it binds to the active site (ATP site) of a variety of kinases in a site specific manner. Therefore, this radical would have a structure known to bind to several kinases. Examples of preferred $R_1$ are the indolinone and 2,4-diamino-5-nitropyrimidine structures of formulas (II) and (III) below wherein $R_3$ and $R_4$ are described herein below.

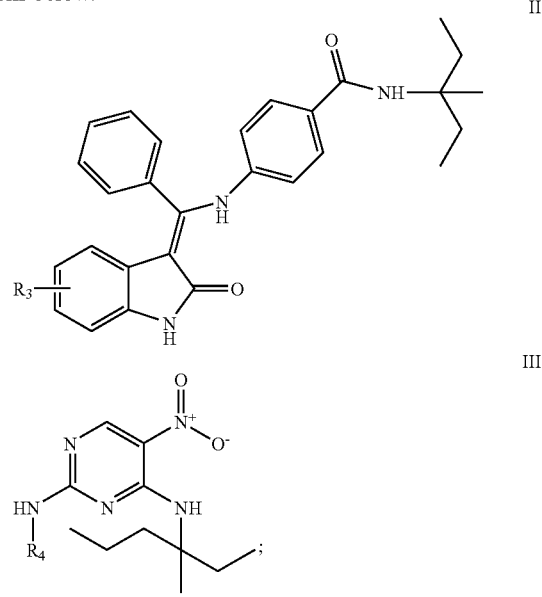

Fluorescent labels suitable for use as in the invention as Y include any of those well known in the art. See, for example, those described in "Handbook of Fluorescent Probes and Research Chemicals" by Richard P. Haugland, Sixth edition (1996). The seventh edition is available on CD-ROM and an updated seventh edition is available on the Web at www.probes.com/handbook/. A number of suitable fluorescent labels are commercially available from Molecular Probes, Inc. It is preferred that the fluorescent label fluoresces at a relatively high wavelength, i.e., above about 450 nm, to avoid interference from cell originating fluorescence and fluorescence originating from test compounds and impurities present in the system or from glass and plastic containers. Accordingly, in one embodiment, the fluorescent label of the invention fluoresces at a wavelength above about 450 nm.

Examples of fluorescent labels useful in the present invention include rhodamine and rhodamine derivatives such as tetramethyl rhodamine, carboxytetramethylrhodamine, Lissamine™ Rhodamine B, Texas Red®, carboxy-X-rhodamine and Rhodamine Red™-X, and other rhodamine derivatives known in the art, fluorescein and fluorescein derivatives such as fluorinated fluoresceins such as Oregon Green® and its derivatives, fluoresceinamine, carboxyfluorescein, alpha-iodoacetamidofluorescein, 4'-aminomethylfluorescein, 4'-N-alkylaminomethylfluorescein, 5-aminomethylfluorescein, 6-aminomethylfluorescein, 2,4-dichloro-1,3,5-triazin-2-yl-aminofluorescein (DTAF), 4-chloro-6-methoxy-1,3,5-triazln-2-yl-aminofluorescein, and fluoresceinisothiocyanate, and other fluorescein derivatives known in the art, 4,4-difluor-4-bora-3a,4a-diaza-s-indacene and its derivatives, cyanine dyes, and the Alexa Fluor® dyes.

More preferred fluorescent labels include fluorescein and fluorescein derivatives such as fluorinated fluoresceins such as Oregon Green® and its derivatives, fluoresceinamine, carboxyfluorescein, alpha-iodoacetamidofluorescein, 4'-aminomethylfluorescein, 4'-N-alkylaminomethylfluorescein, 5-aminomethylfluorescein, 6-aminomethylfluorescein, 2,4-dichloro-1,3,5-triazin-2-yl-aminofluorescein (DTAF), 4-chloro-6-methoxy-1,3,5-triazln-2-yl-aminofluorescein, and fluoresceinisothiocyanate, and other fluorescein derivatives known in the art.

In one embodiment, fluorescent probes of the invention have the following general formula (I):

wherein $R_1$ is a radical of a compound that binds to the active site of a kinase;

L is a direct bond or a $C_1$–$C_{16}$ alkylene group, a $C_2$–$C_{16}$ alkenylene group or a $C_2$–$C_{16}$ alkynylene group, wherein one or more of the available —$CH_2$— groups present in the $C_1$–$C_{16}$ alkylene group, $C_2$–$C_{16}$ alkenylene group or $C_2$–$C_{16}$ alkynylene group is optionally and independently replaced with —O—, —C(O)—, —S(O)$_p$— wherein p is 0 to 2, or —N($R_2$)—;

X is selected from the group consisting of O, S, —N($R_2$)C(O)—, —C(O)N($R_2$)—, —N($R_2$)C(S)—, —C(S)N($R_2$)—, —N($R_2$)C(S)NH—, —NHC(S)N($R_2$)—, —N($R_2$)C(O)NH—, —NHC(O)N($R_2$), —SO$_2$N$R_2$—, —NR$_2$SO$_2$—, —CH$_2$N($R_2$)—, —N($R_2$)CH$_2$—, —CH$_2$S—, —SCH$_2$—, —C(O)CH$_2$S—, —SC(O)CH$_2$—, —NHCH$_2$CH$_2$S—, —SCH$_2$CH$_2$NH—, —NC(O)O—, —ONC(O)—, —C(O)O—, —OC(O)—, NH—N=C($R_2$)—, —C($R_2$)=N—NH—, —NHCH($R_2$)—, and —CH($R_2$)NH—;

$R_2$ is H or $C_{1-3}$alkyl; and

Y is a fluorescent label.

Preferred fluorescent probes are those having formula (I) as described above and wherein:

$R_1$ is an indolinone of formula (II) or a nitropyrimidine of formula (III)

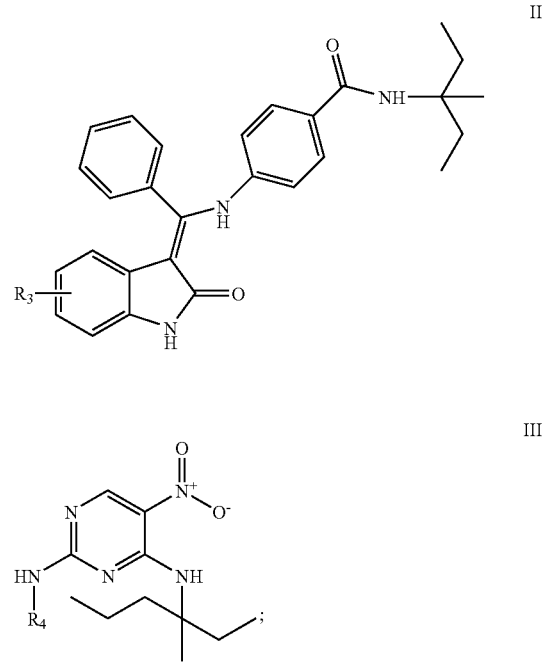

L is a direct bond or a $C_1$–$C_{16}$ alkylene group, a $C_2$–$C_{16}$ alkenylene group or a $C_2$–$C_{16}$ alkynylene group, wherein one to six of the available —$CH_2$— groups present in the $C_1$–$C_{16}$ alkylene group, $C_2$–$C_{16}$ alkenylene group or $C_2$–$C_{16}$ alkynylene group is optionally and independently replaced with —O—, —C(O)— —S(O)$_p$— wherein p is 0 to 2, or —N($R_2$)—;

X is selected from the group consisting of O, S, —N($R_2$)C(O)—, —C(O)N($R_2$)—, —N($R_2$)C(S)—, —C(S)N($R_2$)—, —N($R_2$)C(S)NH—, —NHC(S)N($R_2$)—, —N($R_2$)C(O)NH—, —NHC(O)N($R_2$), —SO$_2$N$R_2$—, —NR$_2$SO$_2$—, —CH$_2$N($R_2$)—, —N($R_2$)CH$_2$—, —CH$_2$S—, —SCH$_2$—, —C(O)CH$_2$S—, —SC(O)CH$_2$—, —NHCH$_2$CH$_2$S—, —SCH$_2$CH$_2$NH—, —NC(O)O—, —ONC(O)—, —C(O)O—, —OC(O)—, —NH—N=C($R_2$)—, —C($R_2$)=N—NH—, —NHCH($R_2$)—, and —CH($R_2$)NH—;

$R_2$ is H or $C_{1-3}$alkyl;

$R_3$ is selected from the group consisting of $C_{1-6}$alkyl, $C_{1-6}$alkoxy, hydroxyC$_{1-6}$alkyl, Cl, F, Br, I, —CN, —CO$_2$H, —CO$_2$C$_{1-6}$alkyl, —S(O)$_2$C$_{1-6}$alkyl, —S(O)$_2$phenyl, SC$_{1-6}$alkyl, —NO$_2$, —OH, —CF$_3$, —N($R_2$)($R_2$), —NHC(O)NHC$_{1-6}$alkyl and —C(O)N($R_2$)($R_2$); and $R_4$ is selected from phenyl and naphthyl and is optionally substituted with one to three groups selected from Cl, F, Br, I, —CH$_3$, —CN, —CO$_2$CH$_3$, —C(O)NR$_5$R$_6$, —NO$_2$, —OH, —NH$_2$, and —CF$_3$—.

The following are specific examples of fluorescent probes falling within the scope of the present invention and are not intended to be limiting in any way:

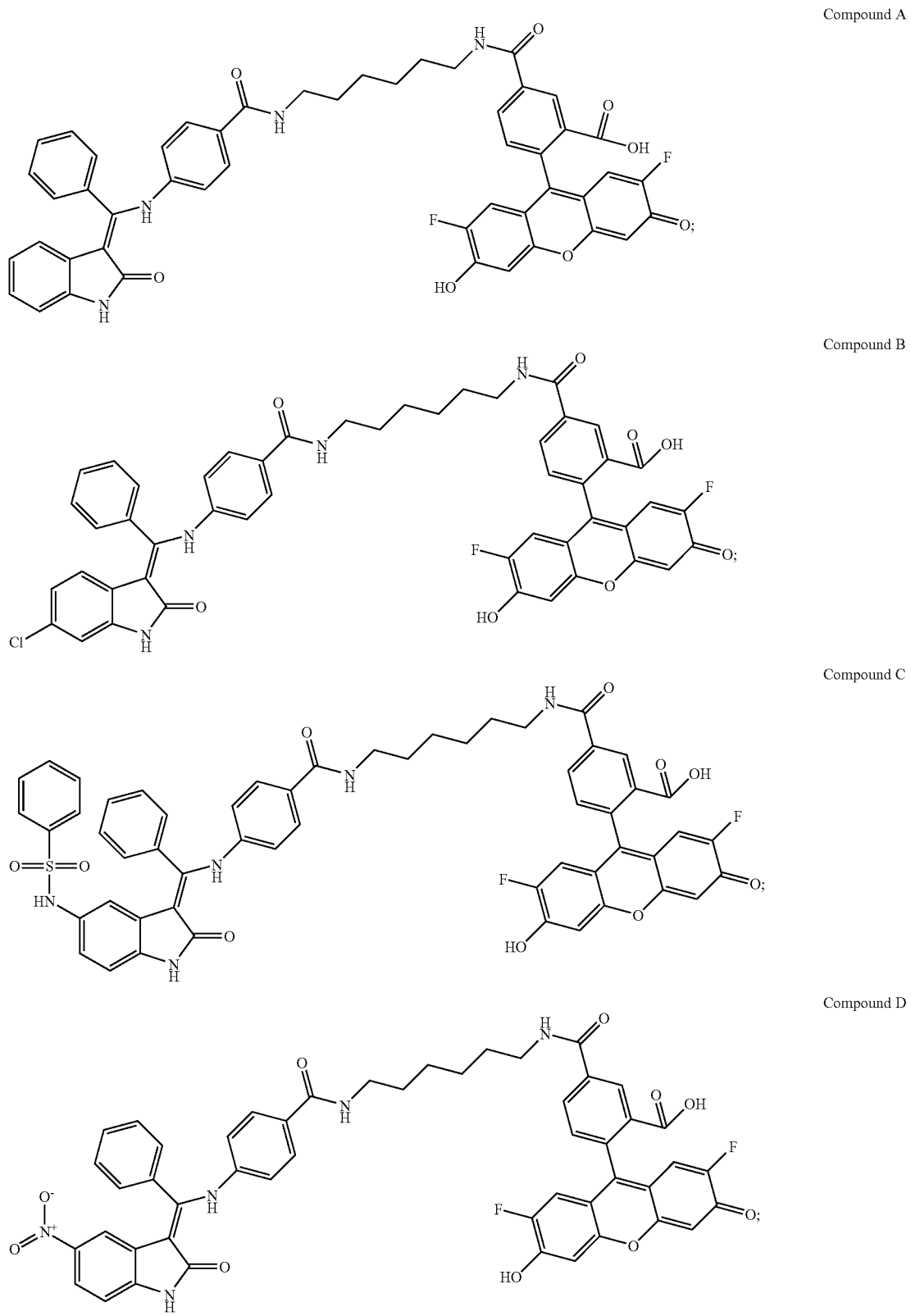

-continued
Compound E
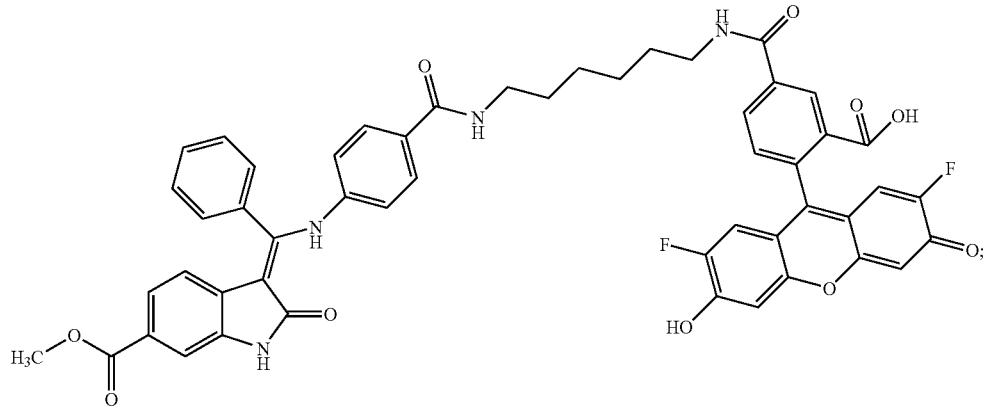
Compound F
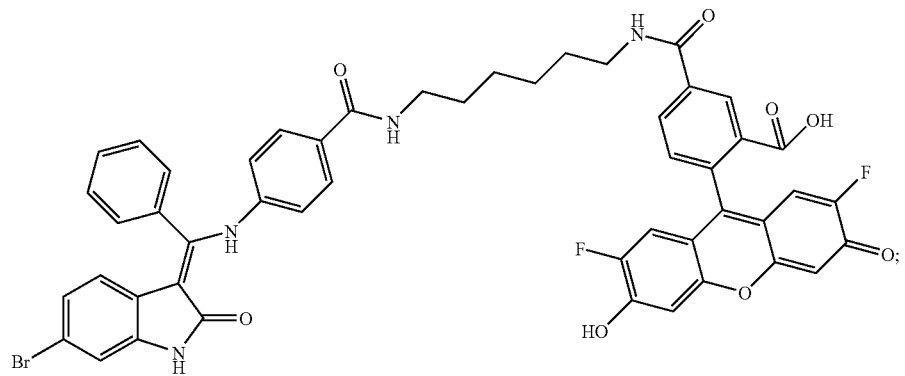
Compound G                    Compound H
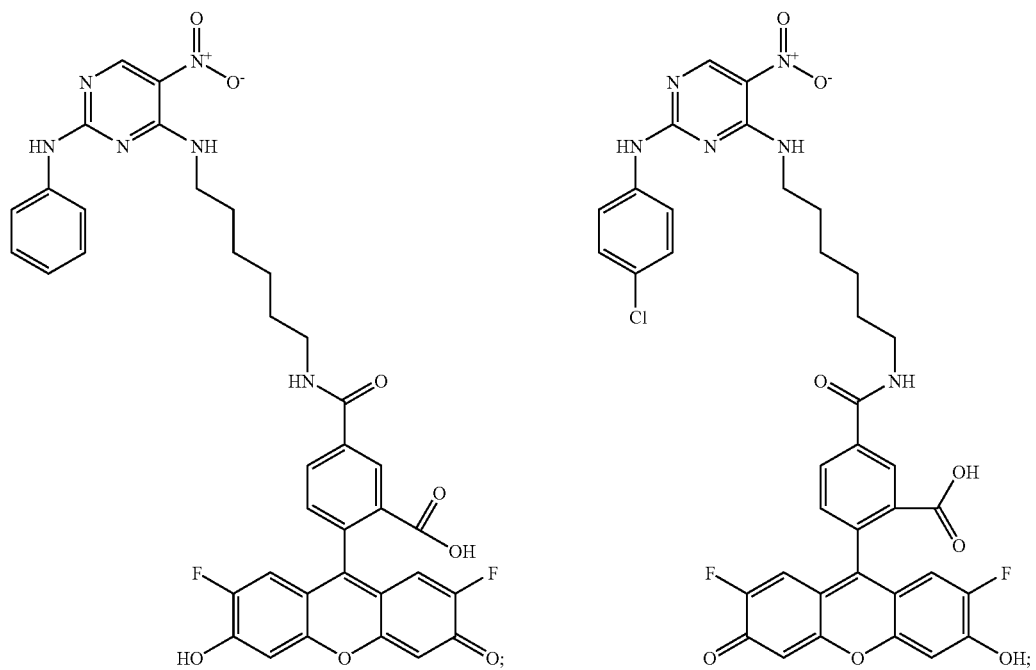

-continued

Compound I

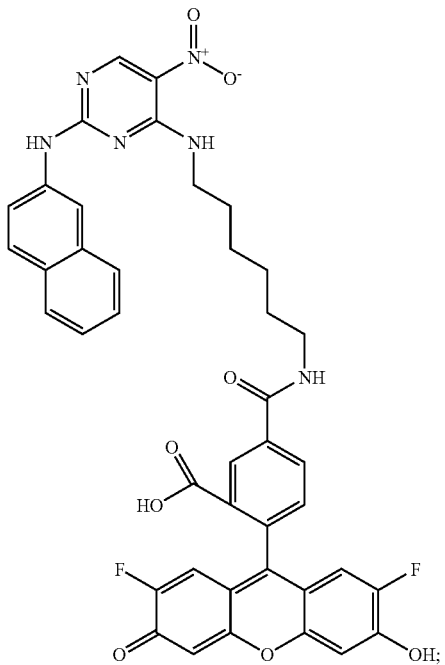

Compound J

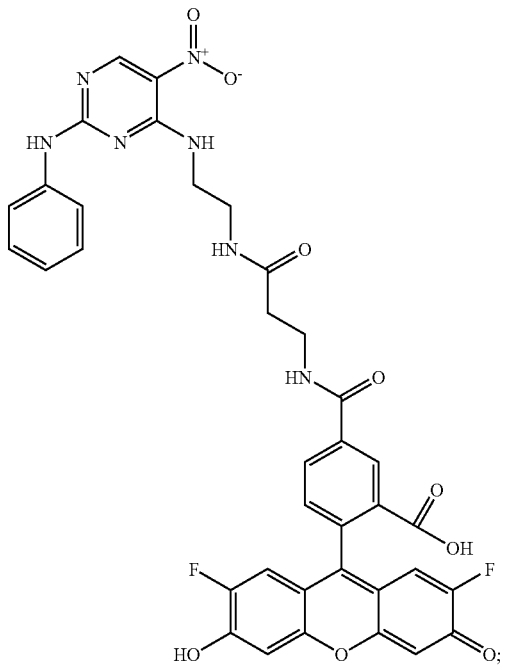

Compound K

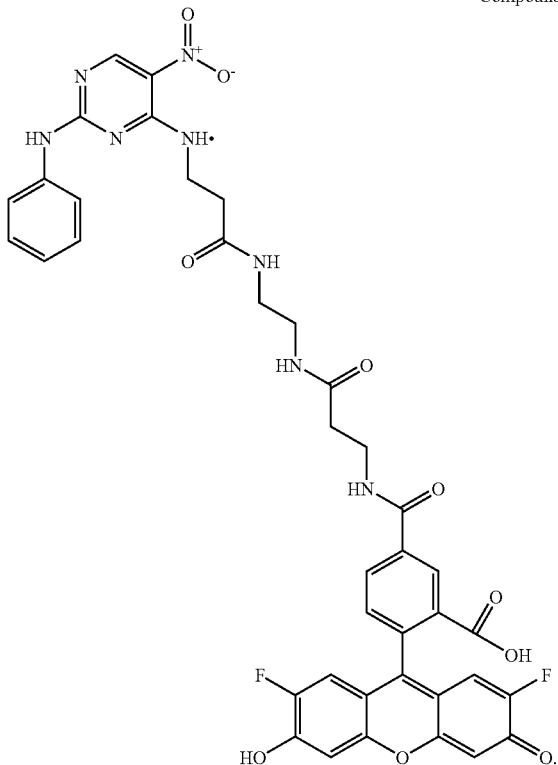

Any fluorescent probes of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the fluorescent probes of the invention can exist in more than one tautomeric form. The invention includes all such tautomers.

The fluorescent probes of the invention are only those which are contemplated to be 'chemically stable' as will be appreciated by those skilled in the art. For example, compounds which would have a 'dangling valency', or a 'carbanion' are not compounds contemplated by the invention.

Methods for the synthesis of the fluorescent probes are provided in the Synthetic Examples section.

II. The Fluorescence Polarization Assay

Fluorescence polarization assays are based on the principle that excitation of a solution of fluorophores with plane polarized light photoselects those fluorophores with excitation dipole moments oriented in parallel relative to the exciting light. The fluorescence emission of these fluorophores will be depolarized to an extent determined by several factors including the rate of diffusion that occurs during the excited state lifetime. This rate, in turn, is determined by several factors, including the volume of the rotating species. Therefore, fluorescence polarization can be applied to the measurement of the interaction between fluorophores and larger molecules.

The novel fluorescent probes disclosed herein can be used in a fluorescence polarization assay to detect and evaluate compounds that bind to the ATP pocket of kinases. It is also understood that the method of the invention can practiced with full length kinases as well as truncated versions of the kinases and hybrid kinases that retain the kinase domain and kinase activity. The invention includes fluorescently labeled probes that can be used in high throughput screening assays for identifying candidate inhibitors to a number of different kinases. In other words the same fluorescent probe can be used in separate high throughput assays for identifying candidate inhitors of kinase A, kinase B etc. The novel fluorescent probes are designed to be both cross reactive across the kinase gene family but specific in their binding to the ATP-binding pocket of a kinase selected from the human kinome. The fluorescence polarization of the probe changes on binding to the kinase domain such that when competed off by an inhibitor the probe polarization measurably decreases. This polarization change serves as the observable in this assay. Unless otherwise specified herein, the conditions that can be employed in running the fluorescence polarization assays of the present invention (e.g., pressure, temperature, pH, solvents, time) may be readily determined by one having ordinary skill in the art.

An assay utilizing the method of the present invention can be designed in the following manner:

(a) Selecting a suitable active site probe-kinase pair by determining the polarization values of free fluorescent probes and of the fluorescent probes bound to a kinase.

(b) Determining the $K_d$ for the fluorescent active site probe-kinase pair.

(c) Demonstrating that the fluorescent probe can be competed from the ATP-binding pocket using ADP, staurosporine or an inhibitor that closely resembles the kinase-binding portion ($R_1$) of the probe.

As a preliminary step, the absorbance, fluorescence excitation and fluorescence emission spectra are determined for each fluorescent probe. The absorbance spectrum is measured in order to avoid inner filter effect. The fluorescence excitation and emission spectra are collected in order to choose the appropriate excitation and emission wavelengths for detecting the probe. These spectra can be determined using any conventional spectrophotometer and fluorimeter with probe in a suitable assay buffer.

In order to identify an appropriate probe for a kinase or kinase domain of interest (step (a)), an initial 4-point titration scheme has been developed. Each kinase is screened against a panel of fluorescent probes. The criteria for a positive selection in this step of the assay are:

i.) acceptable probe fluorescence intensity;
ii.) acceptable polarization change upon binding to kinase;
iii.) acceptable kinase concentration range within which probe binding occurs.

The probe concentration must yield acceptable fluorescence intensities which must be determined for each probe since the quantum yields of different fluorophores vary. The type of 96 or 384-well plate must be carefully determined in order to minimize nonspecific adsorption of the probe to the walls of the wells. Probe adsorption can cause an artificial increase in the measured polarization. Alternatively, a cuvette may be used. The samples are mixed and allowed to incubate for a pre-determined period of time prior to polarization measurement. Instrument settings are defined by the fluorescence characteristics of the probe (excitation spectrum, emission spectrum, quantum yield). The required change in polarization is defined by the instrumentation to be used in the screen. We determined that the minimum change in polarization in this step is 100 milli Polarization units (mP). The required approximate affinity of probe for kinase is defined by protein supply and projected consumption throughout the screening process. When a probe/kinase pair is identified by the process described in step (a), a full equilibrium binding titration is performed in order to determine the equilibrium dissociation constant ($K_d$) describing the interaction (step (b)). The probe is held constant at the pre-determined fixed concentration to each well in a 96 or 384-well plate. Alternatively a cuvette may be used. The kinase of interest is serially diluted to cover a broad concentration range across the plate. The concentration range should cover the concentration where the probe was shown to bind kinase in step a. In addition, several wells should contain either probe alone or probe with the highest concentration of kinase. This is done in order to calculate the $Q_b/Q_f$ ratio for the probe/kinase pair. This is a measure of the total intensity of bound probe ($Q_b$) divided by the total intensity of free probe ($Q_f$), which is necessary to include in the data analysis in order to accurately determine the $K_d$. The $K_d$ can be obtained using conventional methods (e.g., regression analysis).

The criteria for a positive selection in this step of the assay are:

i. Acceptable polarization change upon probe binding to kinase
ii. Acceptable kinase concentration range over which probe binding occurs.

Again, these values are defined by the instrumentation as well as protein supply.

In the next step (c), it is necessary to determine if the interaction is specific and occurring at the ATP binding site of the kinase. This can occur only after the $K_d$ is determined (step (b)) since the choice of kinase concentration is dependent on the total polarization change that occurs upon binding probe. To demonstrate site-specific binding (ATP pocket), inhibitors are used that closely resemble the core chemistry (kinase-binding portion) of the probe. Alternatively, ADP or staurosporine may be used for this application. In this step, ADP, staurosporine or inhibitor is mixed with the fluorescent probe-kinase complex mixture obtained in step (b), and the resulting mixture of fluorescent probe, kinase and ADP is incubated to facilitate competition or other interaction. If the test compound is water-insoluble, it may be necessary to first dissolve the test compound in an appropriate organic solvent, for example DMSO, prior to diluting it in the buffered aqueous solution. The incubation conditions for this step can vary, but generally the incubation is conducted at a temperature of about 25° C. for about 30 minutes. When the difference in fluorescence polarization values obtained in step (c) is negative, i.e., there is a decrease in the polarization in the presence of ADP, staurosporine or test compound, this could indicate that the fluorescent probe is binding to the ATP pocket site on the kinase.

When this step of the invention is run using multiple dilutions of ADP, staurosporine or a test compound, the range of test fluorescence polarization values obtained can be plotted on an appropriate graph. If desired, one may then use conventional methods (e.g., regression analysis) to calculate the equilibrium dissociation constant of the test compound for binding to kinase.

The invention also embodies an assay in which test compounds may be evaluated for the ability to compete with the fluorescent probe domain active site. This is described further in Example 3 below.

Although the preferred method of the invention is to use a fluorescent probe or an environmentally sensitive fluorescent probe. When using an environmentally sensitive probe the change in fluorescent intensity would be measured rather than the change in the fluorescence intensity.

General Synthetic Methods

The fluorescent probes of the invention may be prepared by the methods described below. In each of the methods and schemes described below, the groups $R_1$, L, and X where shown, are as defined above for general formulas I, II and III except as noted. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) if desired. Intermediates and products may be purified by chromatography on silica gel and/or recrystallization. Starting materials and reagents are either commercially available or may be prepared by one skilled in the art using methods described in the chemical literature.

As discussed above, the $R_1$ moiety of formula I can correspond to a structure that binds to the active site of a kinase, such as the structures shown in formulas II and III. For example, compounds of formula I with $R_1$=II may be synthesized as illustrated in Scheme 1 below:

Scheme I

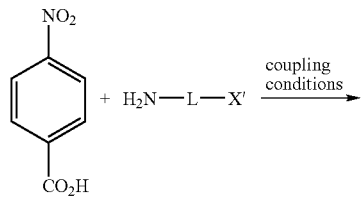

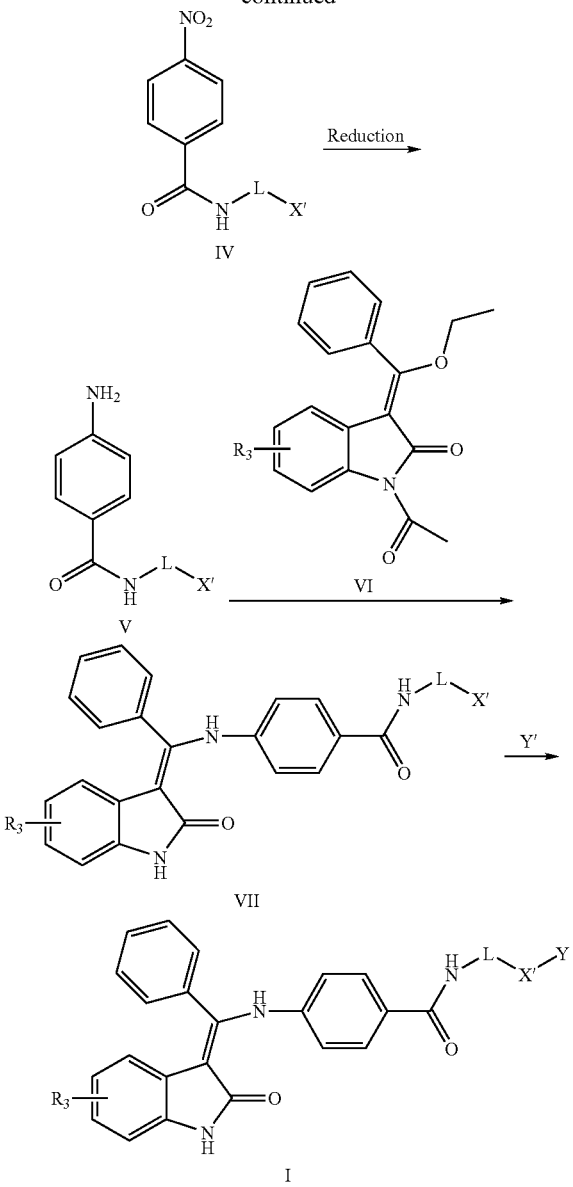

As illustrated above, 4-nitrobenzoic acid is coupled with an amine bearing L and X' to provide intermediate IV. Standard coupling conditions known in the art may be used, for example reaction in a suitable solvent such as methylene chloride in the presence of a coupling agent such as 1-(3-dimethylaminopropyl)-3-ethylcarbodiimide and 1-hydroxybenzotriazole (HOBT) in a suitable solvent such as methylene chloride. The nitro group of IV is then reduced, for example by treatment with hydrogen or a hydrogen source such as ammonium formate in a suitable solvent such as ethanol in the presence of a suitable catalyst such as palladium on carbon. Reaction of V with intermediate VI in a solvent such as DMF while heating at about 75° C. to 120° C. provides intermediate VII. Intermediate VI may be prepared from the optionally substituted 1-acetyl-2-indolinone by refluxing with triethylorthobenzoate in acetic anhydride, followed by hydrolysis of the acetyl group as described by W. Grell et al., U.S. Pat. No. 6,043,254. Reaction of VII with Y', a fluorescent label bearing a functional group that will react with X' provides the desired compound of formula I. X' and Y' and the chemistry to form X—Y are described further below.

Compounds of formula I with $R_1$=III may be prepared as described in Scheme II.

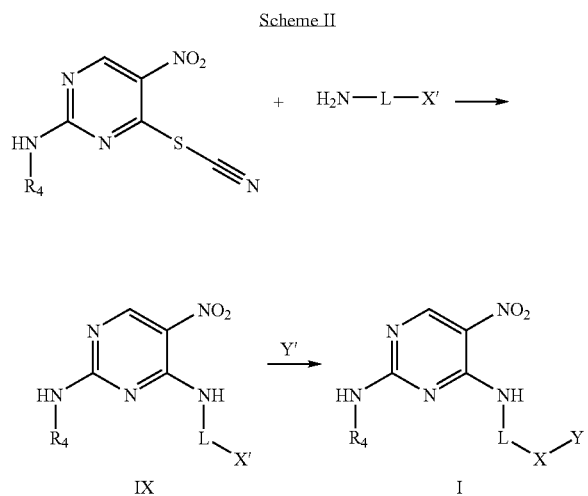

Scheme II

As illustrated above, reaction of the thiocyanate intermediate VIII with $H_2N$-L-X' in a suitable solvent such as methylene chloride provides intermediate IX. Intermediate VIII may be prepared from commercially available 4,6-dichloro-5-nitropyrimidine by reacting with a thiocyanate salt, such as potassium thiocyanate, in a suitable solvent, such as EtOH followed by reaction of the resulting intermediate with $R_4NH_2$ in a suitable solvent, such as EtOH, and in the presence of a base, such as triethylamine. Reaction of IX with Y' provides the desired compound of formula I.

A variety of fluorescent labels suitable as Y are available commercially (see for example Molecular Probes, Inc. at www.probes.com). These labels are available with a variety of reactive functionalities that may be coupled to $R_1$-L-X' to produce the desired $R_1$-L-X—Y. The connecting moiety X obtained will depend on the X' and reactive functionality on Y chosen. For example, in the last step of Scheme I above, a fluorescent label Y having a $CO_2H$ group, i.e., the compound Y—$CO_2H$, (Y') may be reacted with $R_1$-L-X' having an amine functionality for X', i.e., the compound $R_1$-L-$NH_2$, to obtain a compound of formula (I), $R_1$-L-X—Y, wherein X is —NHC(O)—.

Table 1 below shows examples of other reactive functionalities on fluorescent probes that are commercially available and the X group that may be formed by reaction with functional groups X'. Reaction conditions are known to those skilled in the art. Generally they involve combining the fluorescent label containing the reactive functionality (Y') with the desired $R_1$-L-X' in a suitable solvent, such as methylene chloride, ethyl acetate, THF or DMF, optionally in the presence of an appropriate catalyst, as would be known in the art, for example a base such as triethylamine, or a coupling reagent, at a suitable temperature of about −10° C. to the reflux temperature of the solvent, preferably at about 0° C. to room temperature. Particular reaction conditions and reaction times can vary depending on the nature of Y' and $R_1$-L-X'. Reaction progress is easily monitored by methods known in the art such as thin layer chromatography.

TABLE 1

| Y' + $R_1$—L—X' → $R_1$—L—X—Y | | |
|---|---|---|
| Y—N═C═S | $R_1$—L—$NH_2$ | $R_1$—L—NHC(S)N—Y |
| Y—N═C═O[1] | $R_1$—L—$NH_2$ | $R_1$—L—NHC(O)N—Y |
| Y—$SO_2Cl$ | $R_1$—L—$NH_2$ | $R_1$—L—$NHSO_2$—Y |
| Y—CHO | $R_1$—L—$NH_2$ | $R_1$—L—$NHCH_2$—Y[2] |
| Y—$CH_2$—R'(R' = I, Br or Cl) | $R_1$—L—SH | $R_1$—L—$SCH_2$—Y |
| Y—C(O)$CH_2$R'(R' = I, Br or Cl) | $R_1$—L—SH | $R_1$—L—$SCH_2$C(O)Y |
| 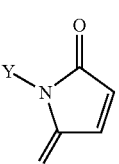 | $R_1$—L—SH | 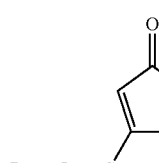 |
| Y—N◁ | $R_1$—L—SH | $R_1$—L—$SCH_2CH_2NH$—Y |
| Y—N═C═O[1] | $R_1$—L—OH | $R_1$—L—OC(O)NH—Y |
| Y—$CO_2H$ | $R_1$—L—OH | $R_1$—L—OC(O)—Y |
| Y—$NHNH_2$ | $R_1$—L—C(O)$R_2$($R_2$ = H or $C_{1-3}$alkyl | $R_1$—L—C($R_2$)═N—NH—Y |
| Y—$NH_2$ | $R_1$—L—C(O)$R_2$($R_2$ = H or $C_{1-3}$alkyl) | $R_1$—L—CH($R_2$)NH—Y[2] |
| Y—$NH_2$ | $R_1$—L—$CO_2H$ | $R_1$—L—C(O)NH—Y |

[1]Readily prepared from the commercially available acyl azide by heating in an organic solvent (Curtius rearrangement). [2]Following reduction of the intermediate imine with a suitable reducing agent such as sodium borohydride.

19

Using the methods described above, one skilled in the art could readily prepare the various fluorescent probes (I) falling within the scope of the present invention.

SYNTHETIC EXAMPLES

The following examples illustrate methods by which the fluorescent probes may be synthesized.

20

Example 1

Synthesis of 6-(2,7-difluoro-6-hydroxy-3-oxo-3H-xanthen-9-yl)-N-{6-[4-({[2-oxo-1,2-dihydro-indol-(3Z)-ylidene]-phenyl-methyl}-amino)-benzoylamino]-hexyl}-isophtalamic acid (Method A) (Comp. A)

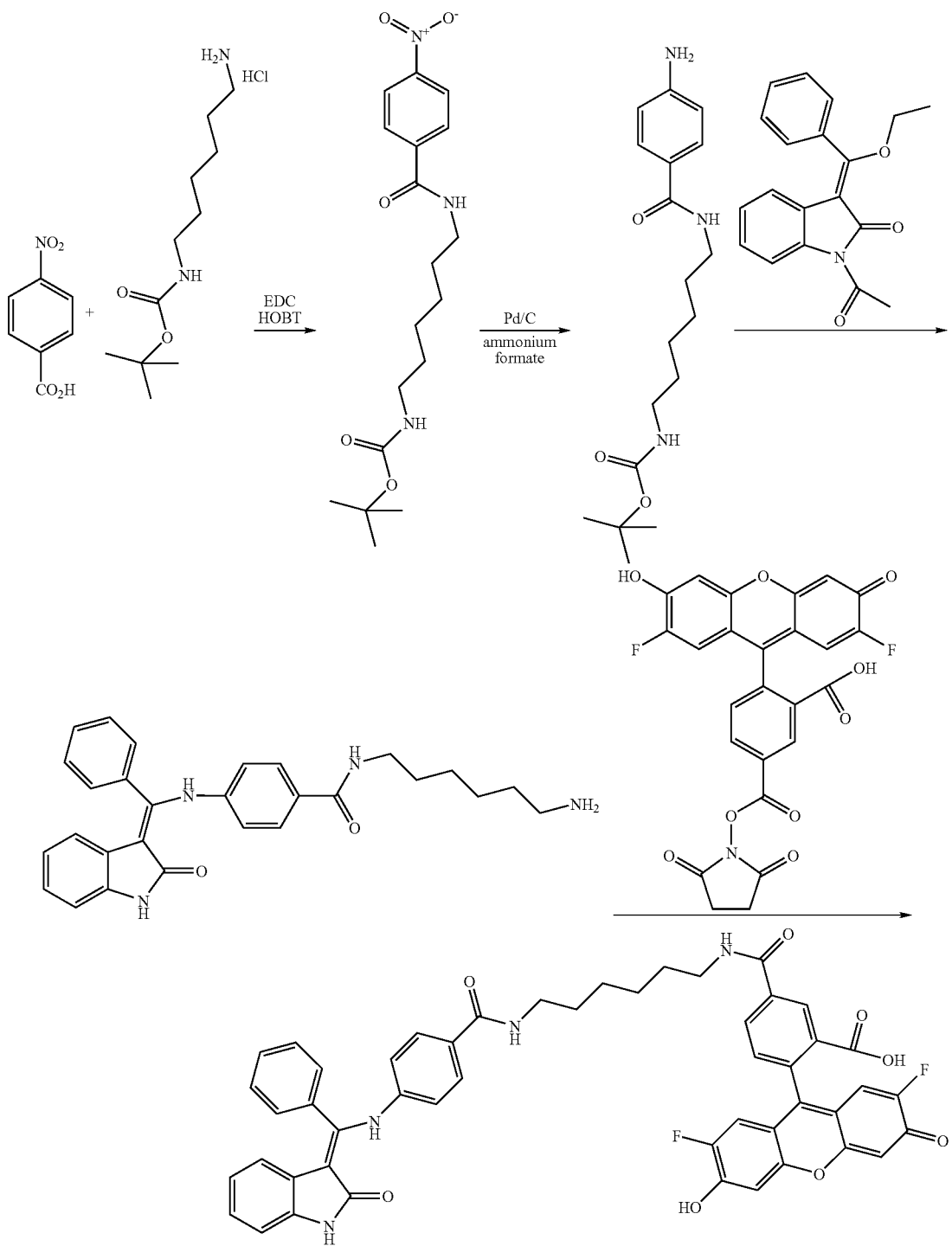

p-Nitrobenzoic acid (500 mg, 2.99 mmol), N-Boc-hexanediame (834 mg, 3.3 mmol), 1-(3-dimethylaminopropyl)-3-ethylcarbodiimide hydrochloride (EDC) (699 mg, 3.65 mmol), and 1-hydroxybenzotriazole hydrate (HOBT) (493 mg, 3.65 mL) were combined in dicloromethane (15 mL) and stirred at ambient temperature for 16 hours. The reaction was diluted with EtOAc (50 mL), washed with water, saturated sodium bicarbonate, and brine. The organic layer was dried over magnesium sulfate and filtered. The organic layer was concentrated by rotary evaporation to collect 1.01 g of [6-(4-nitro-benzoylamino)-hexyl]-carbamic acid tert-butyl ester as a white solid (92% yield).

The above amide (265 mg, 0.750 mmol) was dissolved in EtOH (25 mL). The reaction mixture was charged with ammonium formate (500 mg) and 10% palladium on carbon (100 mg) and stirred for 4 days at ambient temperature. The reaction was filtered through diatomaceous earth and concentrated to recover 265 mg of [6-(4-amino-benzoylamino)-hexyl]-carbamic acid tert-butyl ester as a white crystalline solid (quantitative yield).

1-Acetyl-3-[1-ethoxy-1-phenyl-meth-(Z)-ylidene]-1,3-dihydro-indol-2-one (50 mg, 0.163 mmol) and [6-(4-amino-benzoylamino)-hexyl]-carbamic acid tert-butyl ester (65 mg, 0.195 mmol) were combined in DMF (1 mL) and stirred for 24 hours at 110° C. The DMF was removed by rotary evaporation under high vacuum. The residue was re-dissovled in MeOH (1 mL), a solution of 0.5 M sodium methoxide was added (0.5 mL) and the reaction was stirred at ambient temperature for 1 hour. 4N HCl in dioxane(1 mL) was added and the reaction was stirred overnight. The reaction was concentrated by rotary evaporation. Flash chromatography in a polar gradient of [20% (10% ammonium hydroxide in MeOH) and 80% dichloromethane] provided 60 mg of N-(6-amino-hexyl)-4-({[2-oxo-1,2-dihydro-indol-(3Z)-ylidene]-phenyl-methyl}-amino)-benzamide (82% yield).

N-(6-Amino-hexyl)-4-({[2-oxo-1,2-dihydro-indol-(3Z)-ylidene]-phenyl-methyl}-amino)-benzamide (5 mg, 0.01 mmol) and Oregon green 488 carboxylic acid succinimidyl ester "5-isomer" (5 mg, 0.01 mmol) were dissolved in DMF (1 mL) and shaken for 16 hours at ambient temperature. The reaction was concentrated by rotary evaporation under high vacuum. The residue was loaded onto a preparative TLC plate and eluted with a mobile phase of [30% (10% ammonium hydroxide in MeOH) and 70% dichloromethane]. The title compound (2 mg) was obtained as a bright orange solid (20% yield).

Examples of other probes prepared by Method A are shown below:

Compound B: N-{6-[4-({[6-Chloro-2-oxo-1,2-dihydro-indol-(3Z)-ylidene]-phenyl-methyl}-amino)-benzoylamino]-hexyl}-6-(2,7-difluoro-6-hydroxy-3-oxo-3H-xanthen-9-yl)-isophthalamic acid

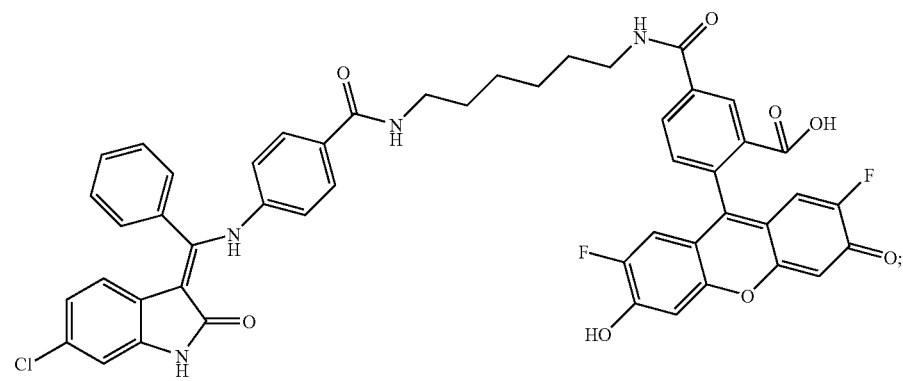

Compound C: N-{6-[4-({[5-Benzenesulfonylamino-2-oxo-1,2-dihydro-indol-(3Z)-ylidene]-phenyl-methyl}-amino)-benzoylamino]-hexyl}-6-(2,7-difluoro-6-hydroxy-3-oxo-3H-xanthen-9-yl)-isophthalamic acid

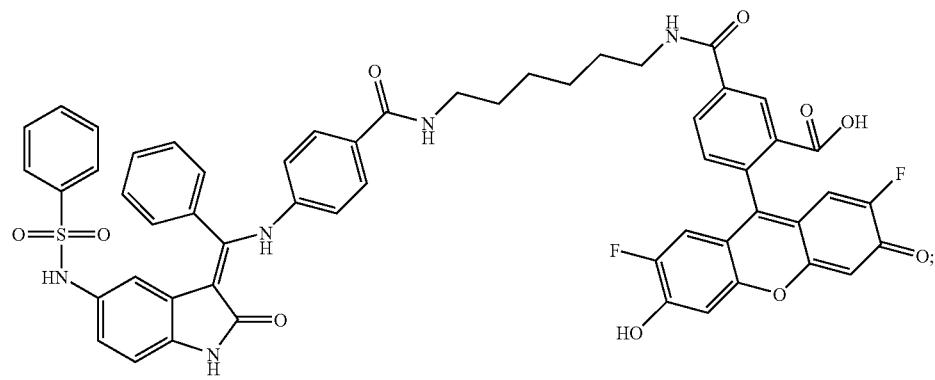

Compound D: 6-(2,7-Difluoro-6-hydroxy-3-oxo-3H-xanthen-9-yl)-N-{6-[4-({[5-nitro-2-oxo-1,2-dihydro-indol-(3Z)-ylidene]-phenyl-methyl}-amino)-benzoylamino]-hexyl)}-isophthalamic acid

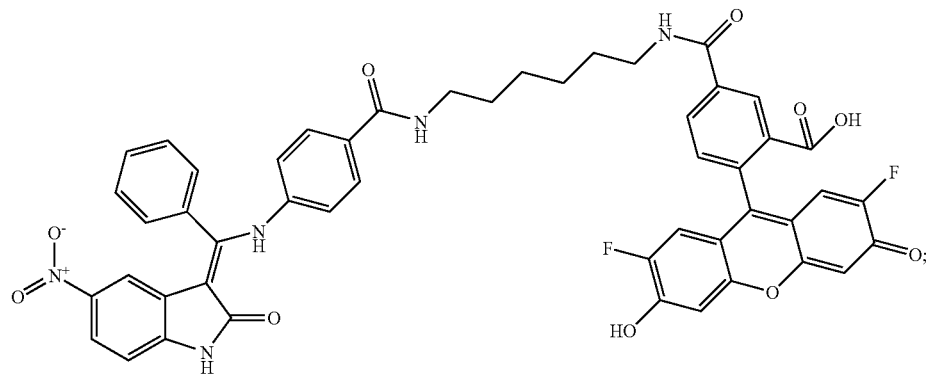

Compound E: 3-[1-(4-{6-[3-Carboxy-4-(2,7-difluoro-6-hydroxy-3-oxo-3H-xanthen-9-yl)-benzoylamino]-hexylcarbamoyl}-phenylamino)-1-phenyl-meth-(Z)-ylidene]-2-oxo-2,3-dihydro-1H-indole-6-carboxylic acid methyl ester

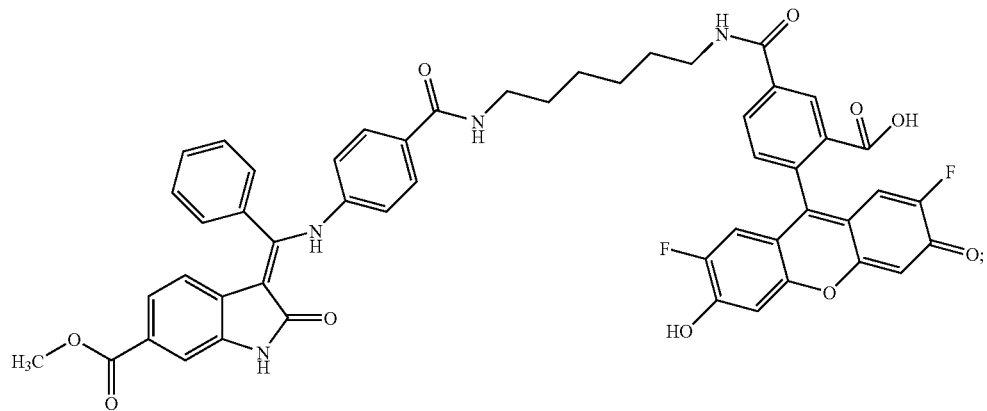

Compound F: N-{6-[4-({[6-Bromo-2-oxo-1,2-dihydro-indol-(3Z)-ylidene]-phenyl-methyl}-amino)-benzoylamino]-hexyl}-6-(2,7-difluoro-6-hydroxy-3-oxo-3H-xanthen-9-yl)-isophthalamic acid

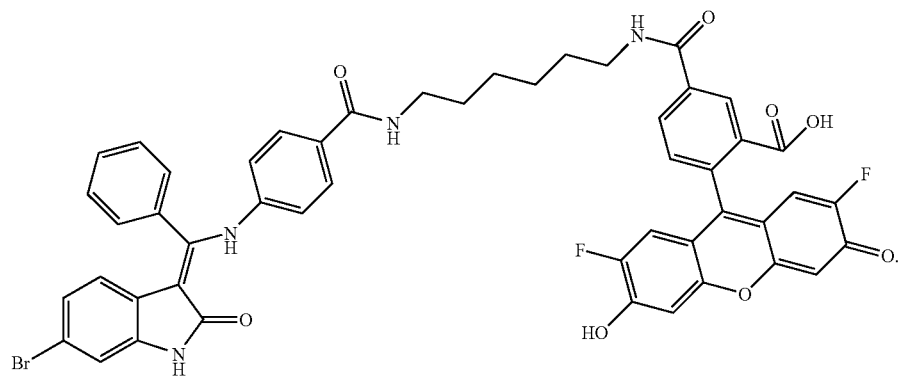

Example 2

Synthesis of 6-(2,7-difluoro-6-hydroxy-3-oxo-3H-xanthen-9-yl)-N-[6-(5-nitro-2-phenylamino-pyrimidin-4-ylamino)-hexyl]-isophthalamic acid (Method B)(Compound G)

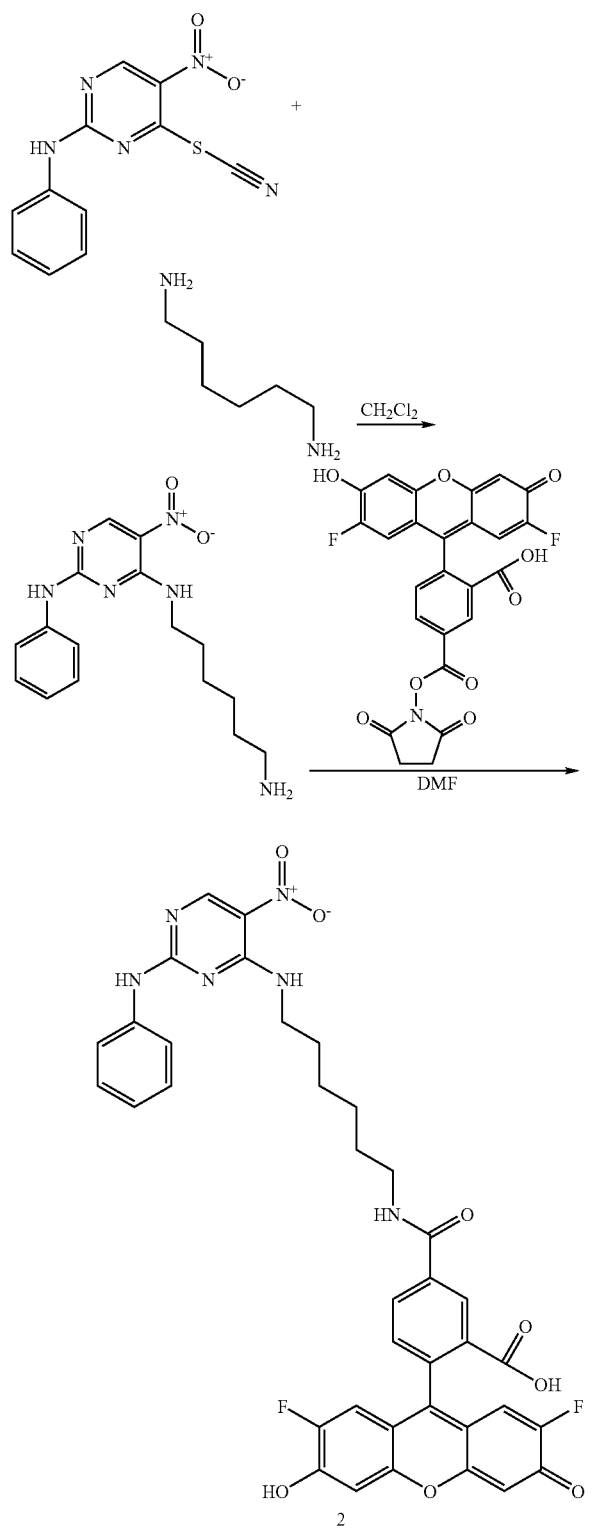

(5-Nitro-4-thiocyanato-pyrimidin-2-yl)-phenyl-amine (85 mg, 0.311 mmol) was dissolved in dichloromethane (3 mL). Hexanediamine was added to the reaction and the mixture was shaken for 16 hours at ambient temperature. The reaction mixture was loaded directly onto a flash chromatography column (silica gel) and eluted with a dichloromethane, MeOH and ammonium hydroxide gradient. $N^4$-(6-Amino-hexyl)-5-nitro-$N^2$-phenyl-pyrimidine-2,4-diamine (80 mg, 78% yield) was isolated as a yellow solid. The above diamine (5 mg, 0.01 mmol) and Oregon green 488 carboxylic acid succinimidyl ester "5-isomer" (5 mg, 0.01 mmol) were dissolved in DMF (1 mL) and shaken for 16 hours at ambient temperature. The reaction was concentrated by rotary evaporation under high vacuum. The residue was loaded onto a preparative TLC plate and eluted with a mobile phase of [30% (10% ammonium hydroxide in MeOH) and 70% dichloromethane]. The title compound was collected as a bright orange solid (7 mg, 64% yield).

Examples of other probes prepared by Method B are shown below:

Compound H: N-{6-[2-(4-Chloro-phenylamino)-5-nitro-pyrimidin-4-ylamino]-hexyl}-6-(2,7-difluoro-6-hydroxy-3-oxo-3H-xanthen-9-yl)-isophthalamic acid

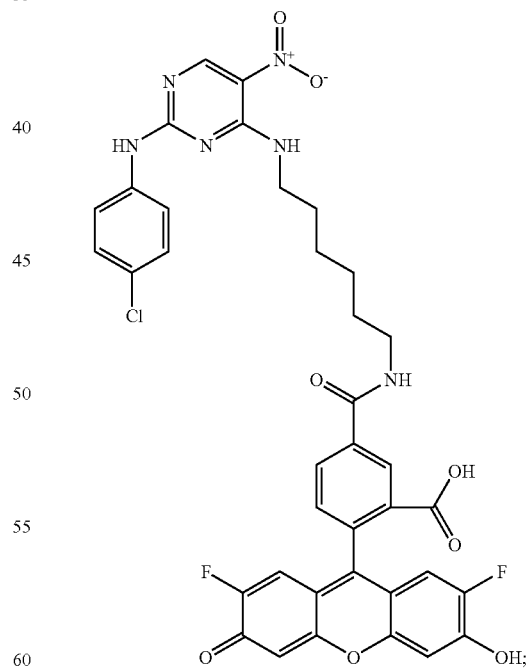

Compound I: 6-(2,7-Difluoro-6-hydroxy-3-oxo-3H-xanthen-9-yl)-N-{6-[2-(naphthalen-2-ylamino)-5-nitro-pyrimidin-4-ylamino]-hexyl}-isophthalamic acid

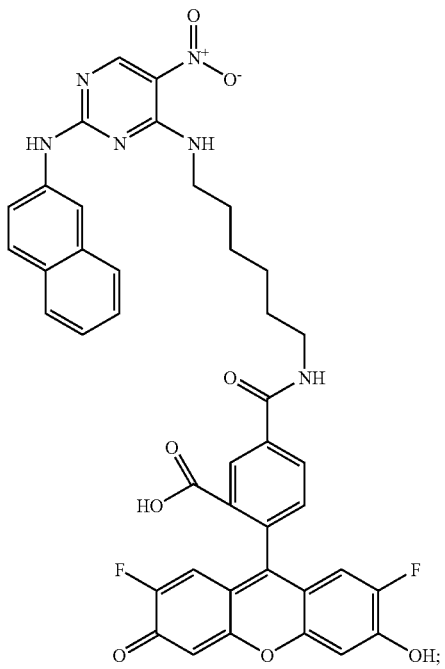

Compound J: 6-(2,7-Difluoro-6-hydroxy-3-oxo-3H-xanthen-9-yl)-N-{2-[2-(5-nitro-2-phenylamino-pyrimidin-4-ylamino)-ethylcarbamoyl]-ethyl}-isophthalamic acid

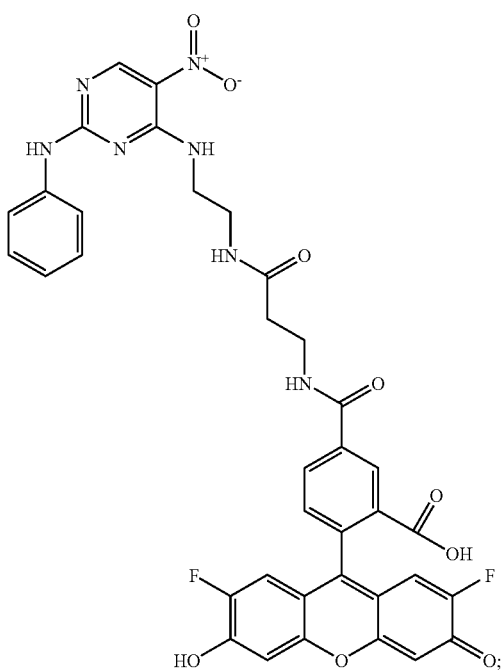

Compound K: 6-(2,7-Difluoro-6-hydroxy-3-oxo-3H-xanthen-9-yl)-N-(2-{2-[3-(5-nitro-2-phenylamino-pyrimidin-4-ylamino)-propionylamino]-ethylcarbamoyl}-ethyl)-isophthalamic acid

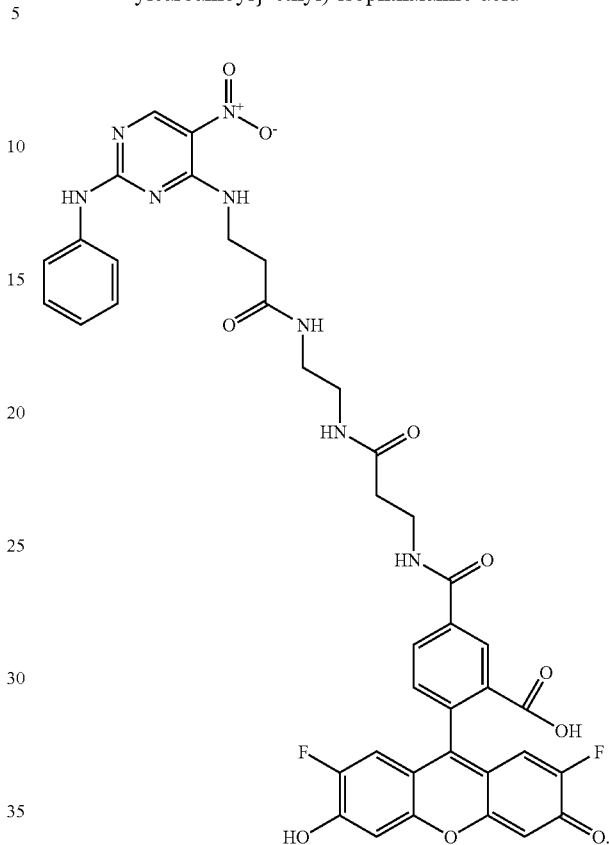

Example 3

Binding Assay for Inhibitors of STK12 Kinase Domain

Step One: Characterization of the Fluorescent Probe

An absorbance spectrum is first evaluated for each probe. The excitation and emission spectra are then measured in order to identify the appropriate excitation and emission wavelengths for detecting the probe. An example of such a probe is 6-(2,7-difluoro-6-hydroxy-3-oxo-3H-xanthen-9-yl)-N-[6-(5-nitro-2-phenylamino-pyrimidin-4-ylamino)-hexyl]-isophthalamic acid where the excitation and emission maxima are 496 nm and 524 nm, respectively. These fluorescence spectra were measured on an SLM-8100 fluorimeter with the probe dissolved in an assay buffer (50 mM HEPES, pH 7.4, 100 mM NaCl, 5 mM $MgCl_2$ 5% Glycerol, 200 mM TCEP and 0.01% (w/v) CHAPS, 2% DMSO).

The affinity of the probe for STK12 kinase domain was then determined in a titration experiment. The polarization assay is carried out in Corning Costar NBS 96-well solid black flat bottom plates. In this example, an LJL Analyst was used with filters appropriate for the excitation/emission characteristics of the fluorescent probe. STK12 kinase domain was serially diluted into wells containing 25 nM probe to cover a broad concentration range across the plate.

In addition, several wells contain either probe alone or probe with the highest concentration of STK12 kinase domain. This is done in order to calculate the $Q_b/Q_f$ ratio for the probe/kinase domain pair. This is a measure of the total intensity of bound probe ($Q_b$) divided by the total intensity of free probe ($Q_f$), which is necessary to include in the data analysis in order to accurately determine the $K_d$. Non-linear least squares regression analysis was used to calculate the equilibrium dissociation constant of the probe from the polarization values obtained for STK12 kinase domain binding to the probe. FIG. 1 shows the results from this titration experiment Step Two: Screening for Inhibitors of Probe Binding:

The plate is set up by first creating a complex between STK12 kinase domain and fluorescent probe 6-(2,7-difluoro-6-hydroxy-3-oxo-3H-xanthen-9-yl)-N-[6-(5-nitro-2-phenylamino-pyrimidin-4-ylamino)-hexyl]-isophthalamic acid that binds to the active site of STK12 kinase domain. In this example, the complex between probe and STK12, was pre-formed in assay buffer (50 mM HEPES, pH 7.4, 100 mM NaCl, 5mM $MgCl_2$, 5% Glycerol, 200 mM TCEP and 0.01% (w/v) CHAPS, 2% DMSO). The concentrations of STK12 kinase domain and probe in this solution were made up such that the final concentration in the assay was 200 nM STK12 kinase domain and 25 nM probe. Test compound was then serially diluted into assay buffer, across the plate. The pre-formed STK12 kinase domain-probe complex was then added to all the wells and incubated for 30 minutes at room temperature. The fluorescence polarization was then measured using a fluorescence polarization plate reader set at the wavelengths appropriate for the fluorescent probe. In this example, an LJL Analyst was used with filters appropriate for the excitation/emission characteristics of the fluorescent probe. Non-linear least squares regression analysis was then used to calculate equilibrium dissociation constants for the test compound, a nitropyrimidine derivate, binding to STK12 kinase domain from the polarization values for the probe binding to STK12 kinase domain in the presence of the test compounds.

Figure 2:
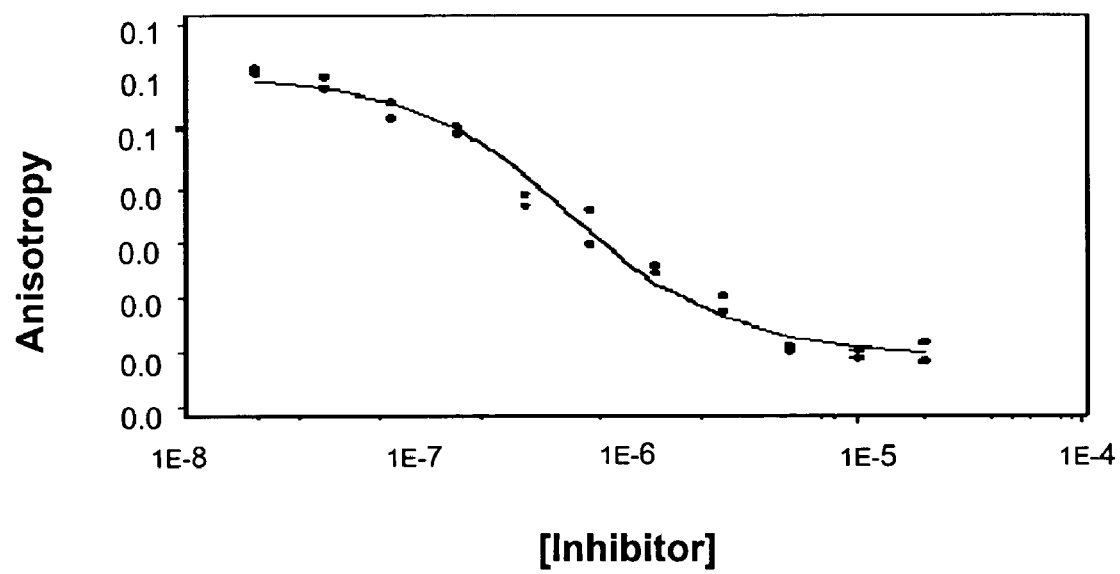
FIG. 2 shows the fluorescence polarization results obtained when screening a test compound for STK12 kinase domain inhibitory activity at various dilutions using fluorescent probe 6-(2,7-difluoro-6-hydroxy-3-oxo-3H-xanthen-9-yl)-N-[6-(5-nitro-2-phenylamino-pyrimidin-4-ylamino)-hexyl]-isophthalamic acid in an assay of the present invention.

FIG. 2 shows the results of a competition assay with 200 nM STK12 kinase domain, 25 nM probe and a competing molecule at various serial dilutions. These results show a decrease in fluorescence polarization of the probe-STK12 kinase domain complex in the presence of the test compound, which is evidence that this test compound is a competitive inhibitor of STK12 kinase domain that competes with fluorescent probe 6-(2,7-difluoro-6-hydroxy-3-oxo-3H-xanthen-9-yl)-N-[6-(5-nitro-2-phenylamino-pyrimidin-4-ylamino)-hexyl]-isophthalamic acid for the STK12 kinase domain active site.

The invention claimed is:

1. A fluorescent probe having the following general formula (I):

$R_1$-L-X—Y  (I)

wherein
$R_1$ is a nitropyrimidine of formula (III):

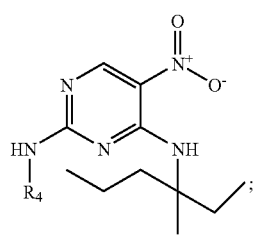

wherein $R_4$ is selected from phenyl and naphthyl and is optionally substituted with one to three groups selected from Cl, F, Br, I, —$CH_3$, —CN, —$CO_2CH_3$, —C(O)$NR_5R_6$, —$NO_2$, —OH, —$NH_2$, and —$CF_3$;

L is a direct bond or a $C_1$–$C_{16}$ alkylene group, a $C_2$–$C_{16}$ alkenylene group or a $C_2$–$C_{16}$ alkynylene group, wherein one or more of the available —$CH_2$— groups present in the $C_1$–$C_{16}$ alkylene group, $C_2$–$C_{16}$ alkenlene group or $C_2$–$C_{16}$ alkynylene group is optionally and independently replaced with —O—, —C(O)—, —S(O)$_p$— wherein p is 0 to 2, or —N($R_2$)—;

X is selected from the group consisting of O, S, —N($R_2$) C(O)—, —C(O)N($R_2$)—, —N($R_2$)C(S)—, —C(S)N ($R_2$)—, —N($R_2$)C(S)NH—, —NHC(S)N($R_2$)—, —N($R_2$)C(O)NH—, —NHC(O)N($R_2$), —$SO_2NR_2$—, —$NR_2SO_2$—, —$CH_2$N($R_2$)—, —N($R_2$)$CH_2$—, —$CH_2$S—, —$SCH_2$—, —C(O)$CH_2$S—, SC(O) $CH_2$—, —$NHCH_2CH_2$S—, —$SCH_2CH_2$NH—, —NC (O)O—, —ONC(O)—, —C(O)O—, —OC(O)—, —NH—N═C($R_2$)—, —C($R_2$)═N—NH—, —NHCH ($R_2$)—, and —CH($R_2$)NH—;

$R_2$ is H or $C_{1-3}$alkyl; and

Y is a fluorescent label which fluoresces at a wavelength above about 450 nm.

2. The fluorescent probe of claim 1 chosen from:

Compound G

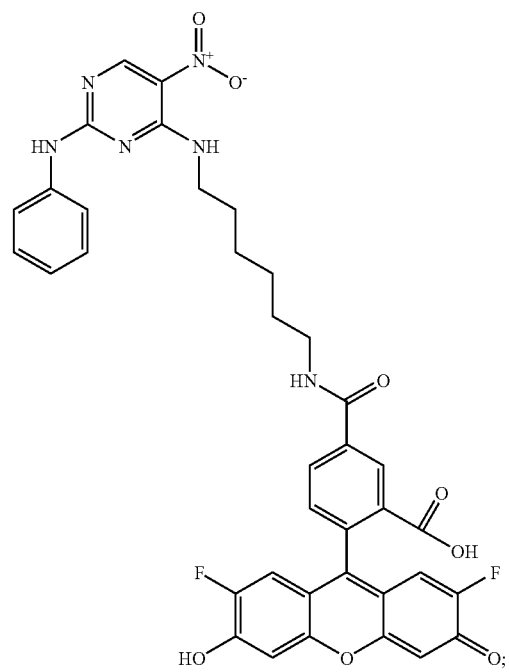

-continued
Compound H
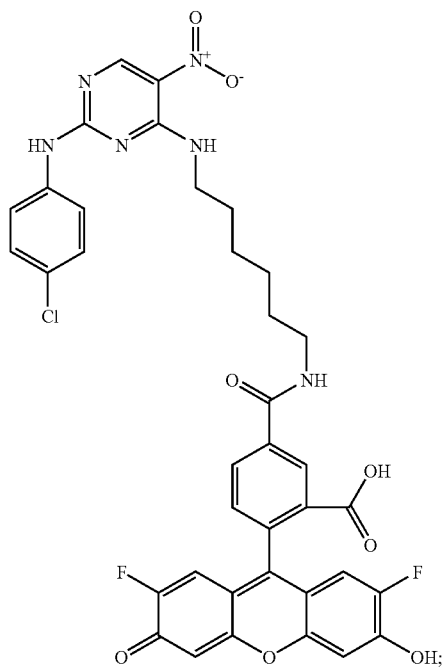
Compound I
Compound J
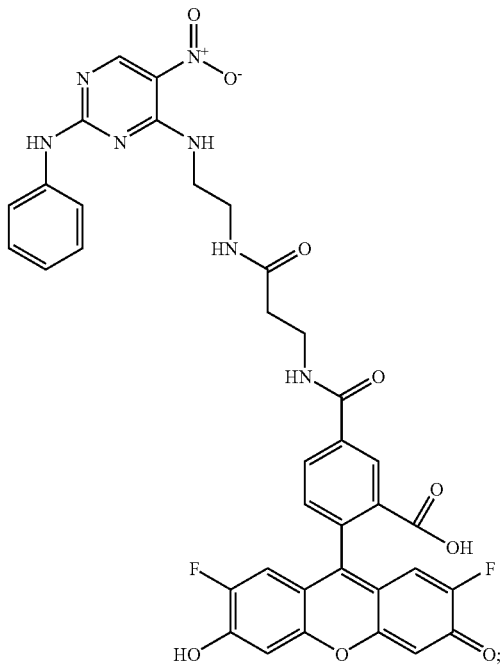
Compound K
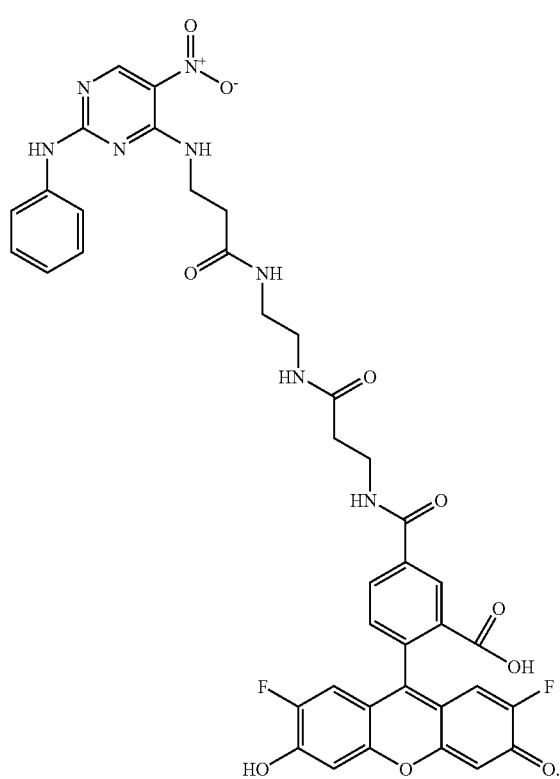

3. A fluorescent probe having the following general formula (I):

R₁-L-X—Y    (I)

wherein
R₁ is a nitropyrimidine of formula (III):

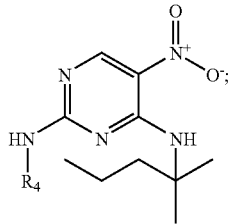

wherein R₄ is selected from phenyl and naphthyl and is optionally substituted with one to three groups selected from Cl, F, Br, I, —CH₃, —CN, —CO₂CH₃, —C(O)NR₅R₆, —NO₂, —OH, —NH₂, and —CF₃;
L is
a direct bond or a $C_1$-$C_{16}$ alkylene group, a $C_2$-$C_{16}$ alkenylene group or a $C_2$-$C_{16}$ alkynylene group, wherein one or more of the available —CH₂— groups present in the $C_1$-$C_{16}$ alkylene group, $C_2$-$C_{16}$ alkenylene group or $C_2$-$C_{16}$ alkynylene group is optionally and independently replaced with —O—, —C(O)—, —S(O)$_p$— wherein p is 0 to 2, or —N(R₂)—;

X is selected from the group consisting of O, S, —N(R₂)C(O)—, —C(O)N(R₂)—, —N(R₂)C(S)—, —C(S)N(R₂)—, —N(R₂)C(S)NH—, —NHC(S)N(R₂)—, —N(R₂)C(O)NHh—, —NHC(O)N(R₂), —SO₂NR₂—, —NR₂SO₂—, —CH₂N(R₂)—, —N(R₂)CH₂—, —CH₂S—, —SCH₂—, —C(O)CH₂S—, —SC(O)CH₂—, —NHCH₂CH₂S—, —SCH₂CH₂NH—, —NC(O)O—, —ONC(O)—, —C(O)O—, —OC(O)—, —NH—N=C(R₂)—, —C(R₂)=N—NH—, —NHCH(R₂)—, and —CH(R₂)NH—;

R₂ is H or $C_{1-3}$alkyl; and

Y is a fluorescent label chosen from rhodamine and rhodamine derivatives, fluorescein and fluorescein derivatives, 4,4-difluor-4-bora-3a,4a-diaza-s-indacene and its derivatives, cyanine dyes, and Alexa Fluor® dyes.

* * * * *